United States Patent [19]

Aungst

[11] Patent Number: 5,091,379

[45] Date of Patent: Feb. 25, 1992

[54] TOPICAL ANTINFLAMMATORY COMPOSITIONS WITH MINIMAL SYSTEMIC ABSORPTION

[75] Inventor: Bruce J. Aungst, Wilmington, Del.

[73] Assignee: Du Pont Merck Pharmaceutical Company, Wilmington, Del.

[21] Appl. No.: 400,404

[22] Filed: Aug. 31, 1989

[51] Int. Cl.$^5$ ............................................. A61K 31/58
[52] U.S. Cl. ................................... 514/159; 514/347; 514/647; 514/772; 514/862; 514/863; 514/864; 514/865; 514/969; 514/975; 548/469; 548/509; 548/510; 424/DIG. 13
[58] Field of Search .............. 424/DIG. 13; 514/647, 514/347, 772, 865, 864, 862, 861, 863, 969, 975, 159, 415; 548/509, 469, 510

[56] References Cited

U.S. PATENT DOCUMENTS

| | | | |
|---|---|---|---|
| 4,473,565 | 9/1984 | Rouee et al. | 514/179 |
| 4,575,515 | 3/1986 | Sandborn | 514/647 |
| 4,833,164 | 5/1989 | Batt | 514/347 |
| 4,895,727 | 1/1990 | Allen | 514/169 |

OTHER PUBLICATIONS

Batt et al., U.S. Patent Application No. 07/293,522.

Primary Examiner—Ronald W. Griffin

[57] ABSTRACT

Topical polyethylene glycol based formulations for the delivery of 2-substituted-1-naphthols and indoles and particularly, 2-phenylmethyl-1-naphthol are provided. Said topical formulations exert excellent localized anti-inflammatory activity while demonstrating low levels of skin penetration in vitro and in vivo thereby reducing unwanted side effects and reducing systemic toxicity associated with the active drug compounds.

41 Claims, No Drawings

TOPICAL ANTIINFLAMMATORY COMPOSITIONS WITH MINIMAL SYSTEMIC ABSORPTION

FIELD OF THE INVENTION

This invention relates to topical formulations for the improved delivery of antiinflammatory agents, particularly 2-substituted-1-naphthols and indoles of the formula (I), said topical formulations comprising active compound and a polyethylene glycol base. These formulations provide minimal systemic absorption of active compound while providing good localized, topical antiinflammatory activity. This invention further relates to the use of these topical formulations to treat inflammatory skin diseases in humans.

BACKGROUND OF THE INVENTION

Co-assigned U.S. patent application Ser. No. 06/839,912 (Batt et al.), incorporated herein by reference, discloses 2-substituted-1-naphthols useful as antiinflammatory agents, said compounds having the formula:

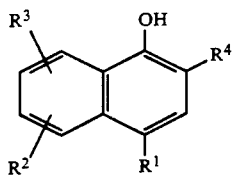

wherein:
$R^1$ is H, $CH_3$, Br, Cl, OH, $OCH_3$, $OC_2H_5$, $COR^{17}$, $COOR^{18}$, $CONR^{19}R^{20}$, phenyl, $-N(R^{12})(R^{13})$,

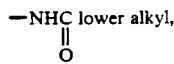

$S(O)_p$ lower alkyl where p is 0, 1 or 2,
or $-NHSO_2$ lower alkyl optionally substituted with F;
$R^2$ and $R^3$ independently are H, $CH_3$, $C_2H_5$, $OCH_3$, or $OC_2H_5$;
$R^4$ is straight-chain or branched alkyl of 1-12 carbons, straight-chain or branched alkenyl of 2-12 carbons, straight-chain or branched alkynyl of 2-12 carbons, cycloalkyl or cycloalkenyl of 5-7 carbons, $CH_2-C\equiv C-(CH_2)_m R^5$ where m is 1-4, $CH=CH-(CH_2)_n R^5$ where n is 0-3 and the olefinic bond has either the Z or E configuration
$A-R^6$, or

A is a chain of 2-6 methylene groups optionally substituted at any one of the methylene carbons by a group $R^8$;
$R^5$ is $C_5-C_7$ cycloalkyl, phenyl, $COOR^9$, $OR^9$, $OC(O)R^9$, or $C(R^{10})(R^{11})OR^9$, with the proviso that if n=0 then $R^5$ is not $OR^9$ or $OC(O)R^9$;
$R^6$ is $C_5-C_7$ cycloalkyl, phenyl, $COOR^9$, $CON(R^{12})(R^{13})$, CHO, CN, $CH(COOR^9)_2$, $C(R^{10})(R^{11})OR^9$, $P(O)(OR^9)_2$, $S(O)_w R^9$ where w is 0-2 with the proviso that if w=1 then $R^9$ is not H;

$SC(NH)NH_2$, $N(R^{12})(R^{13})$, $N_3$, $OR^9$, $OC(O)R^9$, Cl, Br, or I;
$R^7$ is $C_3-C_8$ cycloalkyl

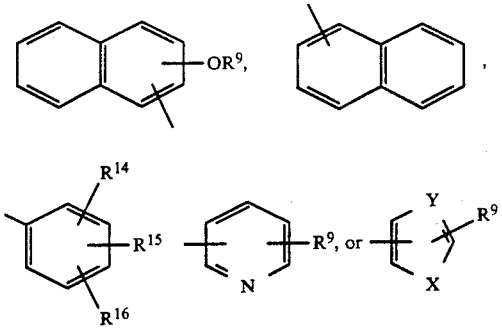

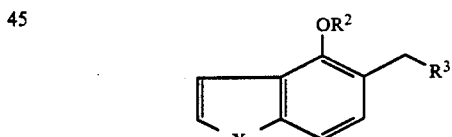

where X is S, O, or $NR^{10}$, and Y is CH or N;
$R^8$ is $C_1-C_4$ alkyl, $C_5-C_7$ cycloalkyl, or phenyl;
$R^9$, $R^{10}$, and $R^{11}$ are independently H or $C_1-C_4$ alkyl;
$R^{12}$ and $R^{13}$ independently are H, $C_1-C_4$ alkyl, or together are $(CH_2)_{4-5}$;
$R^{14}$ is H, $C_1-C_4$ alkyl, $OR^9$, O-phenyl, $OCH_2COOR^9$, O-benzyl, $COOR^9$, $CF_3$, Cl, Br, I, $N(R^{12})(R^{13})$, or $S(O)_w R^9$ where w is 0-2 with the proviso that if w is 1 then $R^9$ is not H;
$R^{15}$ and $R^{16}$ are independently H, $C_{1-4}$ alkyl, $OR^9$, O-benzyl, F, or Cl;
$R^{17}$ is lower alkyl, phenyl optionally monosubstituted with Cl, Br, F, $CH_3O$, $CH_3$, pyridyl, thienyl or furyl;
$R^{18}$ is H or lower alkyl;
$R^{19}$ and $R^{20}$ independently are H or lower alkyl, or taken together are $(CH_2)_{4-5}$; and
$R^{21}$ is H, lower alkyl, phenyl optionally monosubstituted with Cl, Br, F, $CH_3$, $CH_3O$, pyridyl, thienyl, or furyl;
or a pharmaceutically suitable salt thereof.

Co-assigned U.S. patent application Ser. No. 07/293,522 (Batt), incorporated herein by reference, discloses substituted indoles useful as antiinflammatory agents, said compounds having the formula:

wherein:
X is O, S, or $NR^1$;
$R^1$ is H, alkyl of 1-4 carbon atoms, or benzyl;
$R^2$ is H or $C(=O)R^4$;
$R^3$ is pyridyl, 3,4-methylenedioxyphenyl, a 5-membered, aromatic heterocyclic ring with 1 or 2 heteroatoms selected independently from O, S, N or $NR^8$, with the proviso that if two heteroatoms are present then one must be N, and if only one is present it cannot be N; or phenyl optionally substituted with 1-3 groups each selected from F, Cl, Br, alkyl of 1-4 carbon atoms, alkoxy of 1-4 carbon atoms, thioalkyl of 1-4 carbon atoms, alkylsulfonyl of 1-4 carbon atoms, and $NR^6R^7$;
$R^4$ is alkyl or alkoxy of 1-4 carbon atoms;
$R^6$ and $R^7$ independently are H or alkyl of 1-4 carbon atoms, or taken together are $-(CH_2)_4-$; and $R^8$ is H or alkyl of 1-4 carbon atoms.

Further disclosed in these co-assigned applications are topical formulations of the active ingredients useful for treating skin diseases such as psoriasis. However, it has been found that the petrolatum based ointments disclosed therein, result in a high rate of penetration of active ingredient which leads to increased systemic absorption and increased incidence of side effects.

The present invention provides a polyethylene glycol vehicle for the topical administration of the compounds of formula (I) which reduces penetration of active compound but maintains good localized antiinflammatory activity with minimal side effects because of reduced systemic absorption.

SUMMARY OF THE INVENTION

According to the present invention there are provided topical pharmaceutical compositions for the delivery of antiinflammatory compounds of formula (I), useful in the treatment of inflammatory skin diseases. The topical compositions of the present invention have a polyethylene glycol (PEG) vehicle and preferably one or more polyethylene glycols with a molecular weight of greater than or equal to 400.

DETAILED DESCRIPTION

The active antiinflammatory compounds in the topical pharmaceutical compositions of the present invention are 2-substituted-1-naphthols and indoles of the formula:

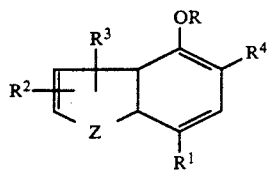

wherein:
Z is $NCH_3$ or $C=C$;
R is $COCH_3$ or H;
$R^1$ is H, $CH_3$, Br, Cl, OH, $OCH_3$, $OC_2H_5$, $COR^{17}$, $COOR^{18}$, $CONR^{19}R^{20}$, phenyl, $-N(R^{12})(R^{13})$,

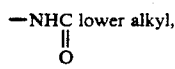

$S(O)_p$ lower alkyl where p is 0, 1 or 2, or $-NHSO_2$ lower alkyl optionally substituted with F;
$R^2$ and $R^3$ independently are H, $CH_3$, $C_2H_5$, $OCH_3$, or $OC_2H_5$;
$R^4$ is straight-chain or branched alkyl of 1-12 carbons, straight-chain or branched alkenyl of 2-12 carbons, straight-chain or branched alkynyl of 2-12 carbons, cycloalkyl or cycloalkenyl of 5-7 carbons,
$CH_2-C\equiv C-(CH_2)_mR^5$ where m is 1-4,
$CH=CH-(CH_2)_nR^5$ where n is 0-3 and the olefinic bond has either the Z or E configuration
$A-R^6$, or

A is a chain of 2-6 methylene groups optionally substituted at any one of the methylene carbons by a group $R^8$;
$R^5$ is $C_5-C_7$ cycloalkyl, phenyl, $COOR^9$, $OR^9$, $OC(O)R^9$, or $C(R^{10})(R^{11})OR^9$, with the proviso that if n=0 then $R^5$ is not $OR^9$ or $OC(O)R^9$;
$R^6$ is $C_5-C_7$ cycloalkyl, phenyl, $COOR^9$, $CON(R^{12})(R^{13})$, CHO, CN, $CH(COOR^9)_2$, $C(R^{10})(R^{11})OR^9$, $P(O)(OR^9)_2$, $S(O)_wR^9$ where w is 0-2 with the proviso that if w=1 then $R^9$ is not H; $SC(NH)NH_2$, $N(R^{12})(R^{13})$, $N_3$, $OR^9$, $OC(O)R^9$, Cl, Br, or I;
$R^7$ is $C_3-C_8$ cycloalkyl

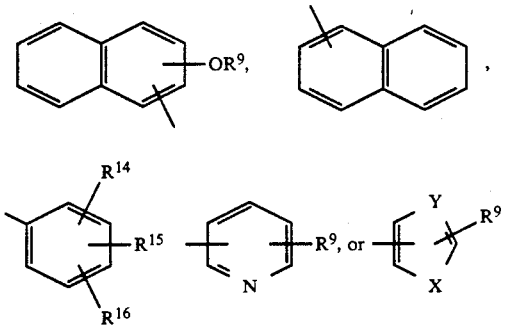

where X is S, O, or $NR^{10}$, and Y is CH or N;
$R^8$ is $C_1-C_4$ alkyl, $C_5-C_7$ cycloalkyl, or phenyl;
$R^9$, $R^{10}$, and $R^{11}$ are independently H or $C_1-C_4$ alkyl;
$R^{12}$ and $R^{13}$ independently are H, $C_1-C_4$ alkyl, or together are $(CH_2)_{4-5}$;
$R^{14}$ is H, $C_1-C_4$ alkyl, $OR^9$, O-phenyl, $OCH_2COOR^9$, O-benzyl, $COOR^9$, $CF_3$, Cl, Br, I, $N(R^{12})(R^{13})$, or $S(O)_wR^9$ where w is 0-2 with the proviso that if w is 1 then $R^9$ is not H;
$R^{15}$ and $R^{16}$ are independently H, $C_{1-4}$ alkyl, $OR^9$, O-benzyl, F, or Cl;
$R^{17}$ is lower alkyl, phenyl, optionally monosubstituted with Cl, Br, F, $CH_3O$, $CH_3$, pyridyl, thienyl or furyl;
$R^{18}$ is H or lower alkyl;
$R^{19}$ and $R^{20}$ independently are H or lower alkyl, or taken together are $(CH_2)_{4-5}$; and
$R^{21}$ is H, lower alkyl, phenyl optionally monosubstituted with Cl, Br, F, $CH_3$, $CH_3O$, pyridyl, thienyl, or furyl;
or a pharmaceutically suitable salt thereof.

Preferred compounds in the topical pharmaceutical compositions of the present invention are those compounds of formula (I) wherein:
$R^4$ is straight-chain or branched alkyl of 1-6 carbons;
allyl optionally substituted on the double bond carbons with methyl or ethyl groups;
cycloalkyl or cycloalkenyl of 5-6 carbons;
$CH_2-C\equiv(CH_2)_mR^5$ where m is 3 and $R^5$ is $COOR^9$ or phenyl;
$CH=CH-(CH_2)_nR^5$ where n is 0-2, the olefinic bond has either the Z or E configuration, and $R^5$ is $COOR^9$, or phenyl;
$A-R^6$; or
$CH_2-R^7$; where
A, $R^6$ and $R^7$ are as defined above, preferably
A is a chain of 2-6 unsubstituted methylene groups;
$R^6$ is phenyl, $COOR^9$, $CON(R^{12})(R^{13})$, CN, $CH(COOR^9)_2$, $C(R^{10})(R^{11})OR^9$, $P(O)(OR^9)_2$, $S(O)_wR^9$, $SC(NH)NH_2$, $N(R^{12})(R^{13})$, $N_3$, $OR^9$, $OC(O)R^9$, Cl, Br, or I;

$R^7$ is as defined above except that X is restricted to S, O, or N—CH$_3$;

$R^{14}$ is as defined above except for O-phenyl, O-benzyl, and $OCH_2COOR^9$;

$R^{15}$ and $R^{16}$ are independently H, $OR^9$, F, or Cl; and w, $R^9$, $R^{10}$, $R^{11}$, $R^{12}$ and $R^{13}$ are as defined above.

More preferred are those preferred compounds wherein $R^1$, $R^2$ and $R^3$ are all H.

Specifically preferred compounds in the topical antiinflammatory pharmaceutical compositions of the present invention are:

a. methyl 7-(1-hydroxy-2-naphthyl)-5-heptynoate
b. ethyl 5-(1-hydroxy-2-naphthyl)-4-pentenoate, Z isomer
c. ethyl 3-(1-hydroxy-2-naphthyl)-proenoate, E isomer
d. 2-(2-propenyl)-1-naphthol
e. ethyl 3-(1-hydroxy-2-naphthyl)-propanoate
f. ethyl 5-(1-hydroxy-2-naphthyl)-pentanoate
g. 2-(5-methylhexyl)-1-naphthol
h. diethyl [3-(1-hydroxy-2-naphthyl)propyl]propanedioate
i. 2-(phenylmethyl)-1-naphthol
j. 2-(3-fluorophenylmethyl)-1-naphthol
k. 2-[(3,4,5-trimethoxyphenyl)methyl]-1-naphthol
l. 2-(2-furylmethyl)-1-naphthol
m. 2-[(3,4-dimethoxyphenyl)methyl]-1-naphthol
n. 2-(2-thienylmethyl)-1-naphthol
o. 2-(3-chlorophenylmethyl)-1-naphthol
p. 2-(4-ethoxyphenylmethyl)-1-naphthol
q. 2-(4-bromophenylmethyl)-1-naphthol
r. 1-methyl-4-hydroxy-5-phenylmethyl indole
s. 1-methyl-4-acetoxy-5-phenylmethyl indole.

The compounds of formula (I) useful in the topical pharmaceutical formulations of the present invention are known to inhibit lipoxygenase. These compounds show excellent antiinflammatory potency in murine models of skin inflammation, and therefore are useful for treating human inflammatory skin diseases, such as psoriasis, chronic eczematous dermatitis, and contact dermatitis. Generally, it is recognized that topical administration of antiinflammatory drugs is preferred in treating these inflammatory skin diseases, since low doses of drug can be applied directly to the diseased skin areas. Ideally such topical formulations should have minimal absorption of the drug into the blood stream. Lower doses and less absorption of drugs used to treat these skin diseases account for fewer and less severe side effects.

It is generally understood that topical formulations which exert high in vitro skin penetration are the most effective in vivo. As early as 1971, Ostrenga et al. (*J. Pharm. Sci.*, 60:1175-1179), demonstrated that in vivo efficacy of topically applied steroids was proportional to the steroid penetration rate through dermatomed human skin in vitro. However, high in vivo skin penetration is also associated with high systemic absorption of active compound and therefore is associated with higher risk and incidence of unwanted side effects and systemic toxicities.

Unlike traditional topical formulations, the PEG based topical formulations of the present invention exert low in vitro and low in vivo skin penetration while surprisingly maintaining good in vivo antiinflammatory activity.

The compounds of formula (I) have a high affinity for PEG. PEGs having a molecular weight (MW) of greater than or equal to 400 can generally be blended to yield formulations with physical characteristics desired for topical vehicles. Therefore, a preferred embodiment of the present invention provides a topical formulation containing active antiinflammatory compound of formula (I) in a PEG base and particularly a PEG 400 base, a PEG 3350 base or a combination thereof. Optionally, the formulations of this invention can have additional excipients for example; preservatives such as methylparaben, propylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

A preferred water-soluble ointment base for the active compounds of formula (I) contains a blend of PEG 400 and PEG 3350, optionally containing additional excipients. Although PEG 400 and PEG 3350 are preferred, other PEGs such as PEGs 200, 300, 600, 900, 1000, 1450, 4500, and 8000 can also be used alone or in a blend containing one or more PEG and optionally additional excipients.

An embodiment of this invention comprises a PEG based pharmaceutical composition containing between about 0.1% w/w to 10% w/w of a compound of the formula I wherein the substituents are as defined above.

A preferred embodiment of this invention comprises a PEG 400 base, PEG 3350 base or a base made of a combination thereof, containing about 0.1% to 10% of a compound of the formula (I) and optionally additional excipients.

The preferred concentration for active compounds of formula (I) is between about 0.1% to 10%. The most preferred concentration is about 1% active compound.

The PEG based topical formulations of the present invention can be in any topical dosage form known to those skilled in the art, including but not limited to: ointment, gels, creams, emulsions, lotions, shampoos, pastes, and sprays. However, the preferred embodiments of this invention are water-soluble ointments containing PEGs, particularly PEG 400, PEG 3350 and/or a combination thereof.

The benefit derived from the topical formulations of the present invention, high antiinflammatory activity with minimal systemic absorption, has not been observed with other commonly used topical agents such as propylene glycols, petrolatum or acetone. There is a need for topical formulations capable of treating inflammatory skin diseases without the risk of systemic absorption and the associated unwanted side effects and toxicities.

The following examples demonstrate the effectiveness of the formulations of the present invention. Parts and percentages are in (w/w) unless otherwise specified.

In vitro Skin Penetration

Rates of the penetration of the compounds of formula (I) were determined by assessing the diffusion through skin or isolated skin layers using Franz diffusion cells; see Current Problems in Dermatology, 7, 58 (1978). The description of Franz diffusion cells and apparatus can be found in publications by the Crown Glass Company. The skin was clamped in the Franz diffusion cells so as to separate a donor chamber from a reservoir chamber. The reservoir was constantly stirred and maintained at 37° C. Generally, the skin surface area was about 1.8 cm$^2$, but when isolated skin layers were used the area was about 1.1 cm². Human skin specimens were generally taken from the thigh and calf areas. Skin was harvested by the supplier, by cutting skin from these areas, to a thickness of about 0.4 mm with a dermatome such as that commercially available from K. C. Assemblage Co. Skin was stored at about $-60°$ C. to 20° C. Based on average skin layer thicknesses, these specimens consisted of stratum corneum, viable epidermis, and part of the dermis. Experiments were also performed using isolated layers of human skin. The stratum corneum layer was isolated from human skin by treating a full skin specimen with 0.5% trypsin for about 1 to 2 hours. Epidermis (which contained intact stratum corneum) and dermis were isolated by immersing a full specimen in 60° C. water for about 1 minute. Skin was also obtained from hairless mice in which inflammation was induced with either arachidonic acid (AA) or tetradecanoylphorbol acetate (TPA).

For most of the vehicles tested, with the exception of acetone, 0.5 ml of each formulation was tested. When acetone was used the amount varied and therefore the amount used is listed in the corresponding tables of data. The acetone vehicles were allowed to dry. For semisolid formulations, an unmeasured amount of the formulations were spread on a gauze pad and applied to the skin. The donor chamber was sealed with parafilm. The reservoir in all the experiments was a 2% solution of bovine serum albumin (Sigma Chemical Co.) and 0.1% $Na_2EDTA$ (Sigma Chemical Co.) in saline. The albumin was added to enhance the solubility of the 5-lipoxygenase inhibitor, so that the concentration gradient could be maintained. The skin penetration rate or flux was calculated from the slope of a linear regressed plot of amount penetrated versus time. The lag time was the x-intercept of the regressed line.

Antiinflammatory Activity in vivo

A biochemical characteristic of skin inflammatory diseases, such as psoriasis, is altered arachidonic acid metabolism with increased production of both prostaglandins and leukotrienes. The compounds of formula (I) and, particularly, 2-phenylmethyl-1-naphthol, are exceptionally potent inhibitors of 5-lipoxygenase. 5-lipoxygenase is known to transform arachidonic acid into 5-5-hydroperoxy-6,8,11,14-eicosatetraenoic acid, the committed step in leukotriene biosynthesis. The 5-lipoxygenase inhibitor appears to interact at the iron site in lipoxygenase.

The compounds of formula (I) and particularly 2-phenylmethyl-1-naphthol (1) was tested in various models of skin inflammation and was found to be very potent in inhibiting the edema induced by the topical application of arachidonic acid (AA), a model in which inflammation is dependent on the production of leukotrienes. The AA model was also used to evaluate and compare PEG ointment formulations containing 2-phenylmethyl-1-naphthol with oil/water cream formulations containing 2-phenylmethyl-1-naphthol. These comparisons are illustrated in Examples 5 to 7.

EXAMPLE 1

Initial experimentation was done to determine how penetration rates of the compounds of formula (I) were influenced by the vehicle and the concentration of the active compound.

Propylene glycol (PG), polyethylene glycol 400 (PEG 400), and petrolatum were examined as potential ingredients in topical formulations. Experiments were also performed with acetone as the vehicle, since this is typically used in topical preclinical pharmacological testing. Results of these studies are shown in Table 1. Flux or skin penetration rate was calculated from the slope of a linear regressed plot of amount penetrated versus time. The lag time was the x-intercept of the regressed line.

TABLE 1

1 Skin Penetration Rates from Various Types of Vehicles

| Vehicle | 1 Concentration | 1 Flux ($\mu g/cm^2$ hr) | Lag Time (hr) |
|---|---|---|---|
| Acetone | 250 mg/ml (0.1 ml) | 6.5 ± 0.9 | 0.04 ± 0.03 |
| Acetone | 100 mg/ml (0.1 ml) | 5.9 ± 0.9 | 0.9 ± 0.1 |
| Acetone | 100 mg/ml (0.25 ml) | 4.9* | 0.6* |
| Acetone | 100 mg/ml (0.5 ml) | 6.9* | 0.5* |
| PG | 5% | 9.2 ± 2.8 | 7.4 ± 4.2 |
| PEG 400 | 5% | 0.2 ± 0.1 | 25.0 ± 6.8 |
| Petrolatum | 0.25% | 0.1* | 0.7 |
| Petrolatum | 1% | 3.0 ± 0.4 | 2.6 ± 6.8 |
| Petrolatum | 5% | 5.6 ± 0.2 | 1.2 ± 0.1 |
| Cream-A** | 0.25% | 2.0 | 1.2 |
| Cream-B** | 1% | 6.2 | 1.1 |
| Cream-C** | 5% | 10.0 | 1.0 |
| Ointment-D** | 1% | 0 | 0 |

*Average of 2 experiments.
**Composition listed below; for the creams, oily (o) and aqueous (w) phases were prepared separately at 60°, mixed and cooled.
(1) is 2-phenylmethyl-1-naphthol

| Formulation | % Composition | | | |
|---|---|---|---|---|
| | A | B | C | D |
| Water (w) | 37 | 36 | 34.5 | |
| Propylene glycol (w) | 12 | 12 | 12 | |
| Sodium lauryl sulfate (w) | 1 | 1 | 1 | |
| Stearyl alcohol (o) | 25 | 25 | 24 | |
| Petrolatum (o) | 25 | 25 | 23.5 | |
| 1 (o) | 0.25 | 1 | 5 | 1 |
| PEG 400 | | | | 49 |
| PEG 3350 | | | | 50 |

At 5% active compound concentrations, the skin penetration rates were in the following order: PG > petrolatum > PEG 400. With acetone as a vehicle, the penetration rate of the inhibitor was independent of the volume or concentration applied. When petrolatum and oil/water cream vehicles were applied, the penetration rate or flux increased with increasing inhibitor concentration, but the increase was not linearly related to concentration. The PEG 400 vehicle provided the lowest penetration rate for active compound thereby providing minimal systemic absorption of active compound.

EXAMPLE 2

Penetration Studies with Formulations Containing Excipients

The penetration rate of the compounds of formula (I) and particularly 2-phenylmethyl-1-naphthol, through human skin was determined for the oil/water cream and PEG ointment which also contained excipients that were added to enhance stability and microbial resistance. Compositions of these formulations are given in Table 2. The results are shown in Table 3.

TABLE 2

Composition of Formulations Containing Excipients

| Formulation | % Composition (w/w) | | | |
|---|---|---|---|---|
| | E | F | G | H |

TABLE 2-continued

| PEG Ointments | | | | |
|---|---|---|---|---|
| 1 | 0.50 | 1.0 | 5.0 | 10.0 |
| PEG 400 | 67.2 | 66.8 | 64.1 | 60.7 |
| PEG 3350 | 30.0 | 29.8 | 28.6 | 27.0 |
| Citric Acid | 0.10 | 0.10 | 0.10 | 0.10 |
| EDTA | 0.02 | 0.02 | 0.02 | 0.02 |
| Water | 2.0 | 2.0 | 2.0 | 2.0 |
| Methyl Paraben | 0.20 | 0.20 | 0.20 | 0.20 |
| Propyl Paraben | 0.015 | 0.015 | 0.015 | 0.015 |

| | % Composition (w/w) | | | |
|---|---|---|---|---|
| Formulation | I | J | K | L |
| Oil/Water Creams | | | | |
| 1 | 0.50 | 1.0 | 5.0 | 10.0 |
| Petrolatum | 27.0 | 27.0 | 27.0 | 22.0 |
| Stearyl Alcohol | 15.0 | 15.0 | 15.0 | 20.0 |
| Stearic Acid | 1.0 | 1.0 | 1.0 | 1.0 |
| Methyl Paraben | 0.20 | 0.20 | 0.20 | 0.20 |
| Propyl Paraben | 0.015 | 0.015 | 0.015 | 0.015 |
| Na Lauryl Sulfate | 1.20 | 1.20 | 1.20 | 1.20 |
| PEG 400 | 5.33 | 5.33 | 5.33 | 5.33 |
| Citric Acid | 0.20 | 0.20 | 0.20 | 0.20 |
| EDTA | 0.04 | 0.04 | 0.04 | 0.04 |
| NaOH | | qs to pH 4.5 | | |
| Water | 49.5 | 49.0 | 45.0 | 39.0 |

TABLE 3

Human Skin Penetration of 1
Using Formulations Containing Excipients

| | 1 Concentration | 1 Flux ($\mu g/cm^2$ hr) | Lag Time (hr) |
|---|---|---|---|
| PEG Ointments | | | |
| E | 0.5% | 0.1 ± 0.1 | ** |
| F | 1.0% | 0.3 ± 0.03 | ** |
| G | 5.0% | 0.3 ± 0.1 | 6.9 ± 4.7 |
| H | 10.0% | 0.4 ± 0.1 | 13.8 ± 3.2 |
| Oil/Water Creams | | | |
| I | 0.5% | 5.8 ± 1.9 | 1.1 ± 0.3 |
| J | 1.0% | 7.4 ± 2.5 | 1.7 ± 1.2 |
| K | 5.0% | 9.3 ± 2.5 | 1.7 ± 1.2 |
| L | 10.0% | 14.7 ± 5.2 | 3.6 ± 1.5 |

**Not determined

The flux or skin penetration from the applied cream was significantly greater than that obtained from the ointment, consistent with those results cited in Example 1 for PEG. Although the flux increased with increasing active compound concentration, the increase was not proportional to concentration.

EXAMPLE 3

Penetration Through Isolated Layers of Human Skin

Diffusion studies using isolated layers of human skin are often useful for determining which layers provide the greatest resistance to drug penetration through skin. Skin penetration rates with 5% active compound ointment and the 5% active compound cream formulations, containing excipients (from Table 2) were evaluated using full skin specimens, isolated stratum corneum, isolated epidermis, isolated dermis, and tape-stripped skin. Tape stripping removes the stratum corneum. The results of these studies are shown in Table 4.

TABLE 4

Rates of 1 Penetration Through Normal Human
Skin, Isolated Skin Layers, or Tape-Stripped Skin
All Experiments were done with skin
from the same 3 donors

| | 1 Flux ($\mu g/cm^2$ hr) | |
|---|---|---|
| Membrane | 5% Ointment-G | 5% Cream-K |
| Normal Skin | 0.4 ± 0.2 | 1.9 ± 0.2 |
| Stratum Corneum | Burst in 1 of 4<br>5.0 ± 1.6 (N = 3) | 2.4 ± 0.4 |
| Epidermis | Burst in 2 of 4<br>1.7 (N = 2) | 2.7 ± 0.3 |
| Dermis | Burst in 6 of 6 | 4.5 ± 2.9 |
| Tape-Stripped (25×) | 3.3 (N = 2) | 2.7 (N = 2) |

Penetration rates through normal skin were higher for the cream than for the PEG ointment. However, flux values with the cream were lower than those previously determined, possible due to intersubject variability of skin permeability. The cream formulation gave similar penetration rates regardless of the membrane layer used. There were differences between normal and isolated (treated) skin when the PEG ointment formulation was used. Each isolated layer had greater permeability than the untreated, full thickness skin specimens. In several experiments, a burst effect was observed, in that the skin layer provided no resistance to drug diffusion into the reservoir. In those experiments, the majority of inhibitor appeared in the reservoir during the first sampling interval. The dermis provided no resistance to penetration when the ointment was applied. It is proposed that the active compounds of formula (I) have a high affinity for the PEG ointment vehicle because of their high solubility in PEG. PEG does not penetrate normal, undamaged skin well, and may hold the active compounds on the surface of the skin or within its outermost layers. However, treating the skin to separate the layers may open the appendages or shunts, allowing the PEG vehicle and the active compound to penetrate simultaneously. Thus, those membranes would have artificially high permeability, not consistent with intact skin in vitro or in vivo.

EXAMPLE 4

Penetration Through Inflamed Hairless Mouse Skin

Studies were performed in which skin inflammation was induced in hairless mice in vivo, and permeability of that skin was evaluated in vitro. The three studies differed in the methods of producing inflammation. A non-inflamed control was run for each. The formulations tested were the oil/water cream and PEG ointment containing excipients (See Table 2) as in the previous example. The effect of skin inflammation on the active compounds penetration are summarized in Table 5. There was no difference between the control and inflamed skin in active compound flux in all studies and for all formulations, except study II with 5% cream. These courses of inflammation did not affect the active compounds skin penetration rates. As with human skin, acetone and cream vehicles consistently gave higher skin penetration rates than the PEG ointment. A comparison of human skin and control hairless mouse skin is given in Table 6.

TABLE 5

Effects of In Vivo Skin Inflammation on In Vitro Skin Penetration of 1

| Skin | Formulation | 1 Flux ($\mu g/cm^2$ hr) | Lag Time (hr) |
|---|---|---|---|
| Study I | | | |
| Control | 5% Ointment-G | 0.2 ± 0.01 | 18.7 ± 2.5 |
| AA Inflamed | 5% Ointment | 0.2 ± 0.03 | 14.5 ± 4.9 |
| Control | 5% Cream-K | 3.3 ± 1.1 | 20.0 ± 3.2 |
| AA Inflamed | 5% Cream | 2.6 ± 1.2 | 18.1 ± 0.3 |
| Control | 25 mg/0.1 ml Acetone | 4.0 ± 0.8 | 10.8 ± 1.7 |
| AA Inflamed | 25 mg/0.1 ml Acetone | 3.7 ± 1.0 | 13.8 ± 1.3 |
| Study II | | | |
| Control | 5% Ointment-G | 0.3 ± 0.02 | 14.0 ± 0.7 |
| TPA Inflamed | 5% Ointment | 0.5 ± 0.05 | 1.2 ± 0.8 |
| Control | 5% Cream-K | 7.0 ± 1.7 | 7.4 ± 2.4 |
| TPA Inflamed | 5% Cream | 1.6 ± 0.06 | 19.3 ± 0.4 |
| Study III | | | |
| Control | 5% Ointment-G | 0.1 ± 0.01 | 10.5 ± 0.9 |
| Chronic TPA Inflamed | 5% Ointment | 0.2 ± 0.1 | 15.8 ± 1.2 |
| Control | 5% Cream-K | 3.2 ± 0.3 | 10.0 ± 1.0 |
| Chronic TPA Inflamed | 5% Cream | 2.6 ± 0.3 | 13.0 ± 3.5 |

AA - Arachidonic acid
TPA - Tetradecanoylphorbol acetate

TABLE 6

Comparison of Human Skin and Control Mouse Skin

| | 1 Flux ($\mu g/cm^2$ hr) | |
|---|---|---|
| Vehicle | Control Mouse Skin | Human Skin |
| 5% Ointment-G | 0.07–0.34 | 0.3 ± 0.1 (Table 3) |
| | | 0.4 ± 0.2 (Table 4) |
| 5% Cream-K | 3.23 ± 6.99 | 9.3 ± 2.5 (Table 3) |
| | | 1.9 ± 0.2 (Table 4) |
| 25 mg/0.1 ml Acetone | 3.95 ± 0.80 | 6.5 ± 0.9 |

EXAMPLE 5

In Vivo Antiinflammatory Activity

Male 18-20 gram CF1 mice were used in these experiments. AA was made up fresh daily in acetone at a concentration of about 100 mg/ml. 10 $\mu l$ of the AA solution (1 mg AA) was applied to the inner surface of the ear to induce swelling. Preliminary data showed that the edema formation followed a time course where maximal edema was formed at about 45-60 minutes and subsided at about 6 hours, and that 1 mg of AA/ear appears to give maximal swelling. Control animals were pretreated about 3 hours before AA application with placebo vehicles (drug free ointment or cream) with 5 mg of vehicle applied to both ears. Drug-treated animals were pretreated about 3 hours before AA application with 5 mg of the vehicle containing active drug, applied to both ears. AA was applied to 1 ear of each mouse. One hour after AA challenge, the animals were euthanized by cervical dislocation and both ears were removed. 6 mm disks were then taken using a skin biopsy punch and weighed. Swelling was determined as the difference between the weights of the AA and vehicle treated ears. Percent inhibition of swelling was calculated as follows:

$$\% \text{ Inhibition} = \frac{(\text{Control swelling} - \text{Drug swelling})}{\text{Control swelling}} \times 100\%$$

Table 7 summarizes the data for PEG ointment and oil/water cream formulations containing various concentrations of active compound. Each data point is the average of 2 experiments with 10 animals per treatment cell.

Although these formulations gave markedly different skin penetration rates at all drug concentrations, they were equipotent in inhibiting AA-induced edema.

TABLE 7

| Cream | | Ointment | |
|---|---|---|---|
| 1 Conc. (%) | % Inhibition | 1 Conc. (%) | % Inhibition |
| 0.5 | 26% | 0.5 | 15% |
| 1 | 60% | 1 | 62% |
| 5 | 86% | 5 | 70% |
| 10 | 87% | 10 | 90% |

EXAMPLE 6

In Vivo Absorption

Approximately 10 mg of 14C-2-phenylmethyl-1-naphthol and 4.99 g of unlabeled 2-phenylmethyl-1-naphthol were used in the preparation of a 100 g 5% ointment or cream. The ointment was a PEG-based ointment and the cream was an oil-in-water emulsion. The specific activities for the ointment and cream were 2.71 and 2.78 uCi/g, respectively. An IV dosing solution (2.5 mg/mL) was prepared prior to dose administration by dissolving radiolabeled 14C-2-phenylmethyl-1-naphthol and unlabeled compound (1:1.5 ratio) in a PEG 400/water (60/40 v/v) solution.

Male Sprague-Dawley rats weighing 240-300 g were used for the studies. Sixteen rats were shaved on the back one day prior to the treatment. Eight of the rats had the application site abraded by a diamond-tipped marker (2 parallel lines and 2 interceding lines). The abrasion penetrated only the stratum corneum, but not the dermis. A 0.5 g dose of 14C-2-phenylmethyl-1-naphthol ointment or cream was applied to an area of approximately 4 $cm^2$ on 4 nonabraded and 4 abraded rats. The treatment site was covered with gauze and occluded with a dental dam. It was further secured by micropore tape and a strip of adhesive elastoplast. Each rat was placed in an open metabolism cage. Urine and feces were collected daily and no detectable radioactivity was found in the urine. Four other rats weighing 270-320 g were given an intravenous dose.

Table 8 shows the percent of dose excreted in rat urine and feces 0-72 hours after the application of 14C-2-phenylmethyl-1-naphthol PEG ointment. Urine accounted for 0.13% and 0.11% of the dose in the nonabraded and abraded rats, respectively, and feces accounted for 0.78% and 0.95% of the dose. There was no difference in the radioactivity excretion between these two skin conditions. The mean total urinary and fecal excretion was only 1% of the administered dose.

TABLE 8

Percent of Dose Excreted in Urine and Feces of 4 Nonabraded and 4 Abraded Rats 0-72 Hrs After the Application of $^{14}$C-1 Ointment

| | Rat No. | Urine | Feces | Total |
|---|---|---|---|---|
| Nonabraded | 1 | 0.05 | 0.65 | 0.70 |
| | 2 | 0.13 | 0.80 | 0.93 |
| | 3 | 0.12 | 0.98 | 1.10 |
| | 4 | 0.20 | 0.68 | 0.88 |
| | Mean | 0.13 | 0.78 | 0.90 |
| | S.D. | 0.06 | 0.15 | 0.16 |
| Abraded | 5 | 0.09 | 0.76 | 0.85 |
| | 6 | 0.14 | 1.26 | 1.40 |
| | 7 | 0.10 | 0.98 | 1.08 |

TABLE 8-continued

Percent of Dose Excreted in Urine and Feces of
4 Nonabraded and 4 Abraded Rats
0–72 Hrs After the Application of
$^{14}$C-1 Ointment

| Rat No. | Urine | Feces | Total |
|---|---|---|---|
| 8 | 0.09 | 0.79 | 0.25 |
| Mean | 0.11 | 0.95 | 1.05 |
| S.D. | 0.02 | 0.23 | 0.25 |

After the application of 14C-2-phenylmethyl-1-naphthol cream to rats, a higher percent of dose was excreted in 0–72 hr urine and feces compared with the PEG ointment. The results are summarized in Table 9. The urine accounted for 1.76% and 2.13% of the dose and the feces accounted for 11.36% and 11.12% of the dose in the nonabraded and abraded rats, respectively. Similar to the ointment application, there was no difference between the nonabraded and abraded rats in radioactivity excretion. A mean total of 13% of the dose was found in the urine and feces.

TABLE 9

Percent of Dose Excreted in Urine and Feces of
4 Nonabraded and 4 Abraded Rats
0–72 Hrs After the Application of
$^{14}$C-1 Cream

| | Rat No. | Urine | Feces | Total |
|---|---|---|---|---|
| Nonabraded | 1 | 2.16 | 11.38 | 13.54 |
| | 2 | 1.74 | 10.64 | 12.38 |
| | 3 | 1.71 | 9.56 | 11.27 |
| | 4 | 1.41 | 13.84 | 15.25 |
| | Mean | 1.76 | 11.36 | 13.11 |
| | S.D. | 0.31 | 1.82 | 1.70 |
| Abraded | 5 | 2.50 | 10.50 | 13.00 |
| | 6 | 1.60 | 11.34 | 12.94 |
| | 7 | 2.23 | 11.67 | 13.90 |
| | 8 | 2.19 | 10.96 | 13.15 |
| | Mean | 2.13 | 11.12 | 13.25 |
| | S.D. | 0.38 | 0.50 | 0.44 |

In order to determine the percent of dose in the ointment or cream that was absorbed percutaneously into the systemic circulation, an IV dose of 14C-2-phenylmethyl-1-naphthol was given to rats. The total radioactivity excreted after the IV dose serves as a reference for evaluation of topical absorption. The excretion results after the IV dose are presented in Table 10. The radioactivity that was recovered in urine and feces accounted for 8.52% and 38.87%, respectively. A total of 47.39% was recovered in 72 hr. The reason for the low radioactivity recovery is unknown. The results of the percutaneous absorption from topical applications are shown in Table 11. The percutaneous absorption from the ointment was about 2% of the applied dose. On the other hand, absorption from the cream was much higher and was about 28% of the dose. The data indicate that the formulation is an important determinant of the extent of 2-phenylmethyl-1-naphthol absorption into the systemic circulation and that the PEG ointment provides for reduced systemic absorption.

TABLE 10

Percent of Dose Excreted in Urine and Feces
of 4 Rats After an IV Dose of 5 mg/kg $^{14}$C-1
(316–360 hr Collection)

| Rat No. | Urine | Feces | Total |
|---|---|---|---|
| 1 | 8.55 | 38.86 | 47.41 |
| 2 | 7.84 | 38.32 | 46.16 |
| 3 | 8.96 | 40.39 | 49.35 |
| 4 | 8.74 | 37.91 | 46.65 |

TABLE 10-continued

Percent of Dose Excreted in Urine and Feces
of 4 Rats After an IV Dose of 5 mg/kg $^{14}$C-1
(316–360 hr Collection)

| Rat No. | Urine | Feces | Total |
|---|---|---|---|
| Mean | 8.52 | 38.87 | 47.39 |
| S.D. | 0.48 | 1.09 | 1.40 |

TABLE 11

Percent of Dose Absorbed Percutaneously from
$^{14}$C-1 Ointment or Cream
Into the Systemic Circulation of Rats

| Skin Condition | Ointment | Cream |
|---|---|---|
| Nonabraded | 1.90% | 27.66% |
| Abraded | 2.22% | 27.96% |

EXAMPLE 7

Skin Penetration with Other 5-Lipoxygenase Inhibitors

Skin penetration studies were also performed with the 5-lipoxygenase inhibitor 1-methyl-4-acetoxy-5-phenylmethyl indole (2) [Compound of Formula I wherein Z is NCH$_3$ and R is COCH$_3$]. 2 hydrolyzes to 1-methyl-4-hydroxy-5-phenylmethyl indole (3) [R is H] in solution and during its course of skin penetration.

In the in vitro skin penetration studies, the sum of 2 and 3 appearing in the reservoir was measured. Solutions containing 2.5% concentration of 2 in propylene glycol or PEG 400 were prepared. Skin penetration rates are listed below.

| Vehicle | Skin No. | Penetration Rate ($\mu$g/cm$^2$ hr) |
|---|---|---|
| PEG 400 | 1 | 0.63 |
| PEG 400 | 2 | 0.40 |
| PEG 400 | 3 | 0.90 |
| Propylene Glycol | 4 | 6.21 |
| Propylene Glycol | 5 | 8.99 |
| Propylene Glycol | 6 | 10.13 |

When tested in the AA ear edema test for topical antiinflammatory potency, these vehicles were equipotent. Therefore the PEG vehicle again demonstrated reduced absorption of active drug while maintaining equipotent antiinflammatory activity.

What is claimed:

1. A topical polyethylene glycol based, water-soluble ointment, which provides minimal systemic absorption of active compound while maintaining effective localized antiinflammatory activity, said composition comprising:
   (a) a polyethylene glycol base comprising one or more polyethylene glycol with a molecular weight of greater than or equal to 400; and
   (b) an antiinflammatory effective amount of a compound of the formula:

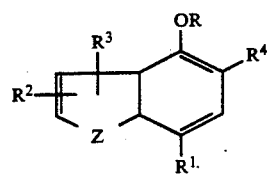

wherein

Z is NCH$_3$ or C=C;
R is COCH$_3$ or H;
R$^1$ is H, CH$_3$, Br, Cl, OH, OCH$_3$, OCH$_2$H$_5$, COR$^{17}$, COOR$^{18}$, CONR$^{19}$R$^{20}$, phenyl, —N(R$^{12}$)(R$^{13}$),

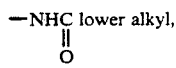

S(O)$_p$ lower alkyl where p is 0, 1 or 2, or —NHSO$_2$ lower alkyl or lower alkyl substituted with F;
R$^2$ and R$^3$ independently are H, CH$_3$, C$_2$H$_5$, OCH$_3$, or OC$_2$H$_5$;
R$^4$ is straight-chain or branched alkyl of 1-12 carbons,
straight-chain or branched alkylenyl of 2-12 carbons,
straight-chain or branched alkynyl of 2-12 carbons,
cycloalkyl or cycloakenyl of 5-7 carbons,
CH$_2$—C≡C—(CH$_2$)$_m$R$^5$ where m is 1-4,
CH=CH—(CH$_2$)$_n$R$^5$ where n is 0-3 and the olefinic bond has either the Z or E configuration
A—R$^6$, or

A is a chain of 2-6 unsubstituted methylene groups or 2-6 methylene group substituted at any one of the methylene carbons by a group R$^8$;
R$^5$ is C$_5$-C$_7$ cycloalkyl, phenyl, COOR$^9$, OR$^9$, OC(O)R$^9$, or C(R$^{10}$)(R$^{11}$)OR$^9$, with the proviso that if n=0 then R$^5$ is not OR$^9$ or OC(O)R$^9$;
R$^6$ is C$_5$-C$_7$ cycloalkyl, phenyl, COOR$^9$, CON(R$^{12}$)(R$^{13}$), CHO, CN, CH(COOR$^9$)$_2$, C(R$^{10}$)(R$^{11}$)OR$^9$, P(O)(OR$^9$)$_2$, S(O)$_w$R$^9$ where w is 0-2 with the proviso that if w=1 then R$_9$ is not H, SC(NH)NH$_2$, N(R$^{12}$)(R$^{13}$), N$_3$, OR$^9$, OC(O)R$^9$, Cl, Br, or I;
R$^7$ is C$_3$-C$_8$ cycloalkyl,

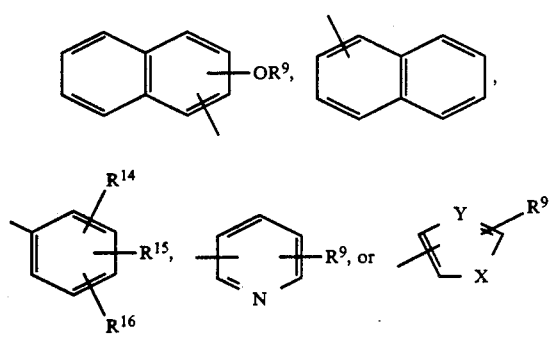

where X is S, O, or NR$^{10}$, and Y is CH or N;
R$^8$ is C$_1$-C$_4$ alkyl, C$_5$-C$_7$ cycloalkyl, or phenyl;
R$^9$, R$^{10}$, and R$^{11}$ are independently H or C$_1$-C$_4$ alkyl;
R$^{12}$ and R$^{13}$ independently are H, C$_1$-C$_4$ alkyl, or together are (CH$_2$)$_{4-5}$;
R$^{14}$ is H, C$_1$-C$_4$ alkyl, OR$^9$, O-phenyl, OCH$_2$COOR$_9$, O-benzyl, COOR$_9$, CF$_3$, Cl, Br, I, N(R$^{12}$)(R$^{13}$), or S(O)$_w$R$^9$ where w is 0-2 with the proviso that if w is 1 then R$^9$ is not H;
R$^{15}$ and R$^{16}$ are independently H, C$_{1-4}$ alkyl, OR$^9$, O-benzyl, F, or Cl;

R$^{17}$ is lower alkyl, phenyl, or phenyl monosubstituted with Cl, Br, F, CH$_3$O, CH$_3$, pyridyl, thienyl or furyl;
R$^{18}$ is H or lower alkyl;
R$^{19}$ and R$^{20}$ independently are H or lower alkyl, or taken together are (CH$_2$)$_{4-5}$; and
R$^{21}$ is H, lower alkyl, phenyl or phenyl monosubstituted with Cl, Br, F, CH$_3$, CH$_3$O, pridyl, thienyl, or furyl;
or a pharmaceutically suitable salt thereof.

2. A composition of claim 1 wherein the base is polyethylene glycol 400.

3. A composition of claim 1 wherein the base is polyethylene glycol 3350.

4. A composition of claim 1 wherein the base is a blend of polyethylene glycol 400 and polyethylene glycol 3350.

5. A composition of claim 1 containing a compound of formula (I) wherein:
R$^4$ is straight-chain or branched alkyl of 1-6 carbons; allyl or allyl substituted on the double bond carbons with methyl or ethyl groups;
cycloalkyl or cycloalkenyl of 5-6 carbons;
CH$_2$—C≡C—(CH$_2$)$_m$R$^5$ where m is 3 and R$^5$ is COOR$^9$ or phenyl;
CH=CH—(CH$_2$)$_n$R$^5$ where n is 0-2, the olefinic bond has either the Z or E configuration, and R$^5$ is COOR$^9$, or phenyl;
A—R$^6$; or
CH$_2$—R$^7$; where
A is a chain of 2-6 unsubstituted methylene groups;
R$^6$ is phenyl, COOR$^9$, CON(R$^{12}$)(R$^{13}$), CN, CH(COOR$^9$)$_2$, C(R$^{10}$)(R$^{11}$)OR$^9$, P(O)(OR$^9$)$_2$, S(O)$_w$R$^9$, SC(NH)NH$_2$, N(R$^{12}$)(R$^{13}$), N$_3$, OR$^9$, OC(O)R$^9$, Cl, Br, or I;
X for the term R$^7$ is restricted to S, O, or N—CH$_3$;
R$^{14}$ is not O-phenyl, O-benzyl, or OCH$_2$COOR$^9$;
R$^{15}$ and R$^{16}$ are independently H, OR$^9$, F, or Cl.

6. A composition of claim 5 wherein the base is polyethylene glycol 400.

7. A composition of claim 5 wherein the base is polyethylene glycol 3350.

8. A composition of claim 5 wherein the base is a blend of polyethylene glycol 400 and polyethylene glycol 3350.

9. A composition of claim 5 wherein R$^1$, R$^2$ and R$^3$ are all H.

10. A composition of claim 9 wherein the base is polyethylene glycol is 400.

11. A composition of claim 9 wherein the base is polyethylene glycol 3350.

12. A composition of claim 9 wherein the base is a blend of polyethylene glycol 400 and polyethylene glycol 3350.

13. A composition of claim 1 wherein the compound is methyl 7-(1-hydroxy-2-naphthyl)-5-heptynoate.

14. A composition of claim 1 wherein the compound is ethyl 5-(1-hydroxy-2-naphthyl)-4-pentenoate, Z isomer.

15. A composition of claim 1 wherein the compound is ethyl 3-(1-hydroxy-2-naphthyl)-propenoate, E isomer.

16. A composition of claim 1 wherein the compound is 2-(2-propenyl)-1-naphthol.

17. A composition of claim 1 wherein the compound is ethyl 3-(1-hydroxy-2-naphthyl)-propanoate.

18. A composition of claim 1 wherein the compound is ethyl 5-(1-hydroxy-2-naphthyl)-pentanoate.

19. A composition of claim 1 wherein the compound is 2-(5-methylhexyl)-1-naphthol.

20. A composition of claim 1 wherein the compound is diethyl [3-(1-hydroxy-2-naphthyl)propyl]propanedioate.

21. A composition of claim 1 wherein the compound is 2-(phenylmethyl)-1-naphthol.

22. A composition of claim 1 wherein the compound is 2-(3-fluorophenylmethyl)-1-naphthol.

23. A composition of claim 1 wherein the compound is 2-[(3,4,5-trimethoxyphenyl)methyl]-1-naphthol.

24. A composition of claim 1 wherein the compound is 2-(2-furylmethyl)-1-naphthol.

25. A composition of claim 1 wherein the comound is 2-[(3,4-dimethoxyphenyl)methyl]-1-naphthol.

26. A composition of claim 1 wherein the compound is 2-(2-thienylmethyl)-1-naphthol.

27. A composition of claim 1 wherein the compound is 2-(3-chlorophenylmethyl)-1-naphthol.

28. A composition of claim 1 wherein the compound is 2-(4-ethoxyphenylmethyl)-1-naphthol.

29. A composition of claim 1 wherein the compound is 2-(4-bromophenylmethyl)-1-naphthol.

30. A composition of claim 1 wherein the compound is 1-methyl-4-hydroxy-5-phenylmethyl indole.

31. A composition of claim 1 wherein the compound is 1-methyl-4-acetoxy-5-phenylmethyl indole.

32. A composition of claim 21 wherein the base is polyethylene glycol 400.

33. A composition of claim 21 wherein the base is polyethylene glycol 3350.

34. A composition of claim 21 wherein the base is a blend of polyethylene glycol 400 and polyethylene glycol 3350.

35. A composition of claim 30 wherein the base is polyethylene glycol 400.

36. A composition of claim 30 wherein the base is polyethylene glycol 3350.

37. A composition of claim 30 wherein the base is blend of polyethylene glycol 400 and polyethylene glycol 3350.

38. A composition of claim 31 wherein the base is polyethylene glycol 400.

39. A composition of claim 31 wherein the base is polyethylene glycol 3350.

40. A composition of claim 31 wherein the base is blend of polyethylene glycol 400 and polyethylene glycol 3350.

41. A method of treating an inflammatory skin disease in a mammal comprising administering to the mammal any of the compositions of claims 1, 2–5, 6–9, 10–31, 32–34, 35–37 and 38–41.

* * * * *